US00PP15185P3

(12) United States Plant Patent
Hancock

(10) Patent No.: US PP15,185 P2
(45) Date of Patent: Sep. 28, 2004

(54) BLUEBERRY PLANT DENOMINATED 'AURORA'

(50) Latin Name: *Vaccinium corymbosum*
Varietal Denomination: Aurora

(75) Inventor: James F. Hancock, East Lansing, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 10/350,345

(22) Filed: Jan. 23, 2003

(65) Prior Publication Data

US 2004/0148671 P1 Jul. 29, 2004

(51) Int. Cl.[7] ..... A01H 5/00

(52) U.S. Cl. ..... Plt./157

(58) Field of Search ..... Plt./157

*Primary Examiner*—Anne Marie Grunberg
*Assistant Examiner*—S B McCormick-Ewoldt
(74) *Attorney, Agent, or Firm*—Harness, Dickey & Pierce, P.L.C.

(57) ABSTRACT

Aurora is a new blueberry variety of *Vaccinium corymbosum*. It is a productive, very late ripening variety with high fresh market quality intended for areas where northern highbush varieties are grown successfully. Plants of Aurora are vigorous and upright. Canes are numerous, moderately branched and the fruit are well exposed. Its berries are moderately large, have small, dry picking scars, excellent powder-blue color, delicious flavor and excellent firmness. Aurora has a harvest season that begins about 5 days after the variety known as 'Elliott.'

2 Drawing Sheets

Latin name and variety denomination: The present invention relates to a new and distinct variety of *Vaccinium corymbosum,* which is hereby denominated 'Aurora.'

CROSS-REFERENCE TO RELATED APPLICATIONS

This application is related to the present inventor's United States Patent Applications entitled "Blueberry plant denominated 'Liberty,'" U.S. patent application Ser. No. 10/350,343, filed Jan. 23, 2003, and "Blueberry plant denominated 'Draper,'" U.S. patent application Ser. No. 10/350,354, filed Jan. 23, 2003. Both of these applications are also assigned to the assignee of the present application. The disclosures of the above applications are hereby incorporated herein by reference.

SUMMARY OF THE INVENTION

The present invention relates to a new and distinct variety of highbush blueberry plant, denominated 'Aurora.' Aurora is a new blueberry variety of *Vaccinium corymbosum* from the Michigan State University breeding program. It is a productive, very late ripening variety with high fresh market quality that is intended for areas where northern highbush varieties are grown successfully. Plants of Aurora are vigorous and upright. Canes are numerous, moderately branched and the fruit are well exposed. Its berries are moderately large, have small, dry picking scars, excellent powder-blue color, delicious flavor and excellent firmness. Aurora has a harvest season that begins about 5 days after the variety known as 'Elliott.' 'Aurora' ripens 10–14 days after 'Brigetta'. Blueberry growers often receive their highest profits in the late season. Aurora will provide a new late ripening option with high quality fruit.

Emasculated flowers of the 'Brigetta' highbush blueberry from Australia were pollinated in 1991 with pollen from the northern highbush variety Elliott. The seeds were germinated, grown in a greenhouse for 1 year and then field planted at Benton Harbor, Mich. Aurora was selected from a group of 54 siblings in 1997. The original selection has been evaluated at Benton Harbor, Mich. annually for 11 years. Asexual reproduction took place at East Lansing, Mich. and Lowell, Oreg. Aurora has been propagated by hardwood cuttings that produced over a hundred shoots that were rooted in the greenhouse and then planted in the field. Initiation of rood development from hardwood cuttings takes about two to about three months. In addition, Aurora has been propagated by softwood cuttings that have been rooted. Furthermore, generation of microshoots in a greenhouse using established tissue culture methods has produced thousands of clones of Aurora. Initiation of root development from microshoots takes about three to about four weeks. Such methods are discussed in the following references, which are incorporated by reference in their entirety: Doran, W. L. and Bailey, J. S. "Propagation of the high bush blueberry by softwood cuttings," Bulletin Massachusetts Agricultural Experiment Station; no. 410. Amherst, Mass. Massachusetts State College, 1943; Doehlert, C. A. "Propagating blueberries from hardwood cuttings," Circular (New Jersey Agricultural Experiment Station) 490. New Brunswick, N.J. New Jersey Agricultural Experiment Station, 1945; Doehlert, C. A. "Propagating blueberries from hardwood cuttings," Circular (New Jersey Agricultural Experiment Station) 551. New Brunswick, N.J.: New Jersey Agricultural Experiment Station, 1953; El Shiekh, A.; Wildung, D. K.; Luby, J. J.; Sargent, K. L,; Read, P. E. "Long term effects of propagation by tissue culture or softwood single node cuttings on growth habit, yield, and berry weight of 'Northblue' blueberry," Journal of the American Society for Horticultural Science. 1996, 121:2, 339 342; Galletta, G. J.; Ballington, J. R.; Daubeny, H. A.; Brennan, R. M.; Reisch, B. J.; Pratt, C.; Ferguson, A. R.; Seal, A. G.; McNeilage, M. A.; Fraser, L. G.; Harvey, C. F.; Beatson, R. A.; Hancock, J. F.; Scott, D. H.; Lawrence, F. J.; Janick, J. (ed.); Moore, J. N. "Fruit breeding. Volume II. Vine and small fruits," Department of Horticulture, Purdue University, West Lafayette, Ind. 1996 John Wiley and Sons; New York; USA; Strik, B.; Brun, C.; Ahmedullah, M.; Antonelli, A.; Askham, L.; Barney, D.; Bristow, P.; Fisher, G.; Hart, J.; Havens, D. Draper A. D. and Chandler C. K. "Accelerating highbush blueberry selection evaluation by early propagation," Journal of the American Society for Horticultural Science. 1986 111(2): 301–303; Pritts M. P. and Hancock J. F. (Eds.) "Highbush blueberry production guide," Northeast Regional Agricultural Engineering Service, Ithaca, N.Y. USA 1992.

Clones of Aurora have been tested for two years at Grand Junction, Mich., South Haven, Mich., Lacota, Mich., Corvallis, Oreg., and Lowell, Oreg. In all cases all resulting plants have stably displayed characteristics of the variety. Consistent high yields at Benton Harbor and Grand Junction, Mich. indicate that the buds and wood of Aurora are tolerant to fluctuating late fall and spring temperatures. Aurora also has excellent winter hardiness, as it has routinely been challenged with mid-winter temperatures below–20° C. Probable areas of adaptation and markets include blueberry growers in Michigan and across the USA, Canada, Argentina, Australia, Chile, France, Germany, and New Zealand.

BRIEF DESCRIPTION OF THE DRAWINGS

The present invention will become more fully understood from the detailed description and the accompany drawings, wherein.

DETAILED BOTANICAL DESCRIPTION

Figure 1:
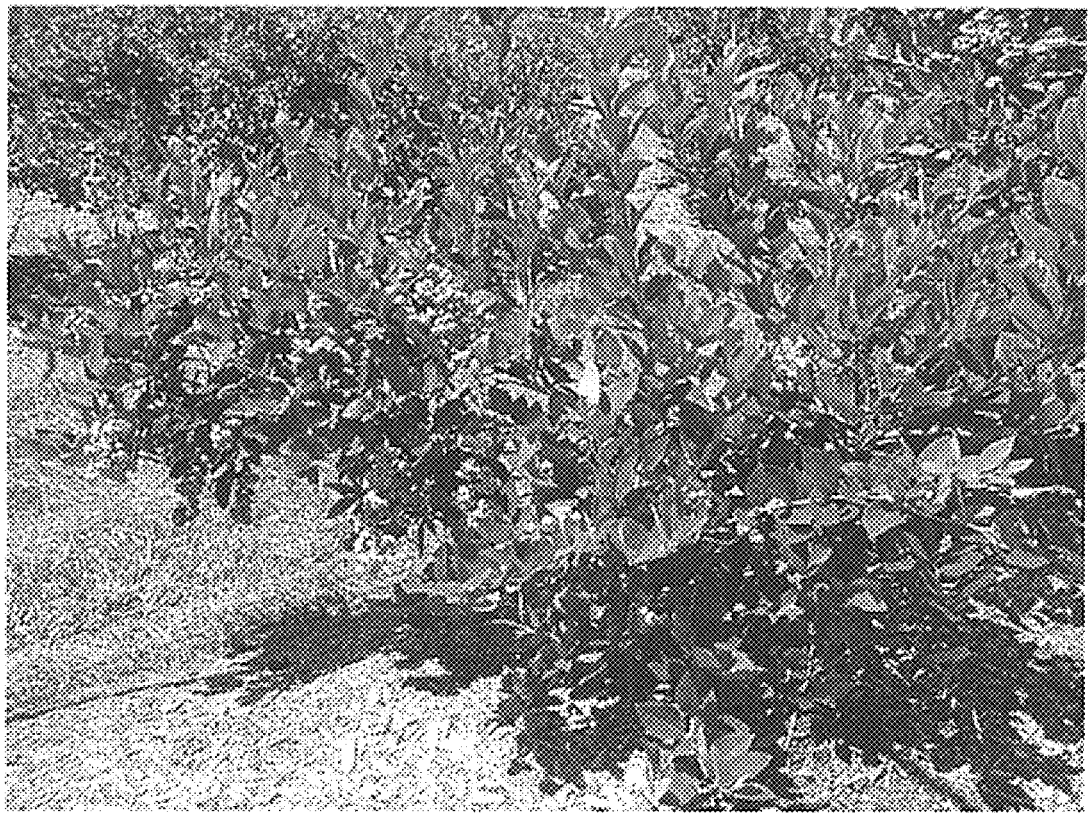
FIG. 1 is a photographic print in full color showing, in the foreground, an exemplary 4-year-old Aurora blueberry plant. The plants appearing in the background are of a different variety and are not part of the Aurora blueberry plant, nor is the grass appearing in the picture part of the Aurora blueberry plant.
Figure 2:
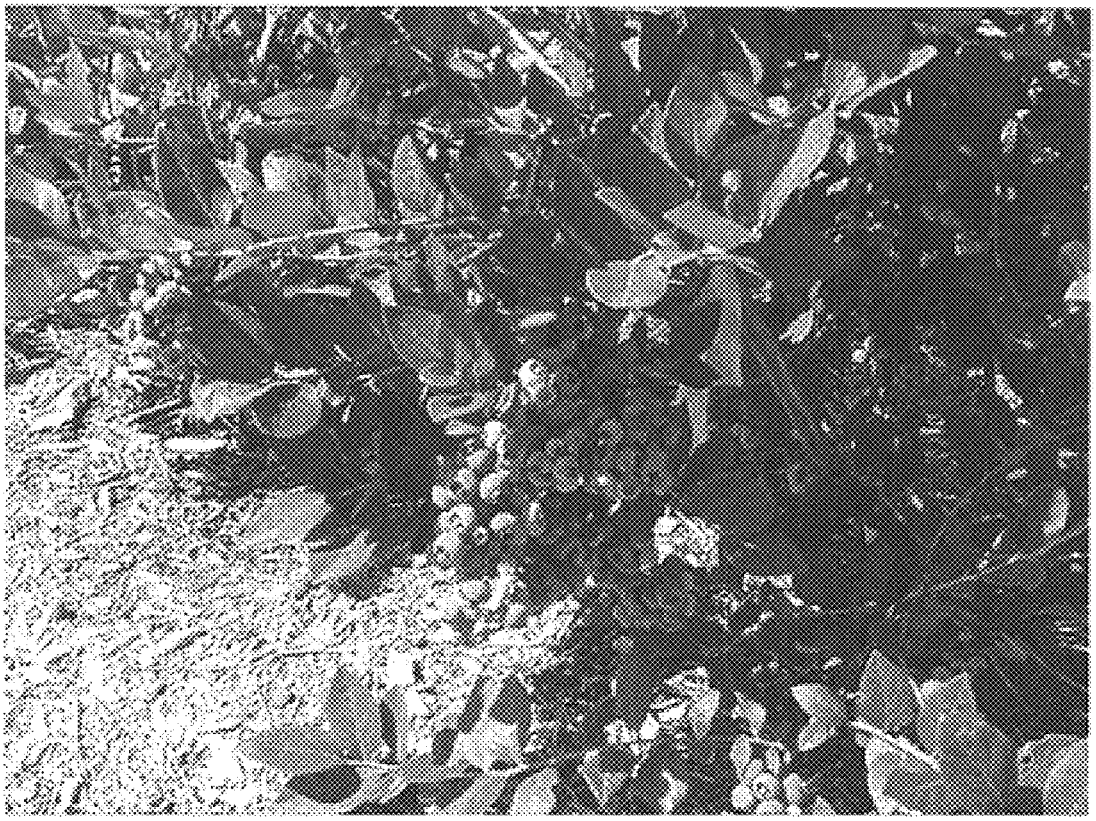
FIG. 2 is a photographic print in full color illustrating exemplary fruit clusters of a 4-year-old Aurora blueberry plant. Some of the fruit is not yet mature and does not show the characteristic mature color.

The following is a detailed botanical description of the new and distinct variety of blueberry, its flowers, fruit and foliage, based on observations of specimens grown at Benton Harbor Mich., Grand Junction, Mich., South Haven, Mich., Lacota, Mich., Corvallis, Oreg., and Lowell, Oreg., over a two year period. The taxonomic characteristics chosen in the detailed description are standard in the practice (R E Gough, R J Hindle, and V G Shutak, "Identification of Ten Highbush Blueberry Cultivars using Morphological Characteristics," *HortScience* 11 (5): 512–4, 1976). Color descriptions, except those given in common terms, are presented in Royal Horticultural Society Colour Chart designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table I are applicable only to mature fruit.

Aurora requires pollination for fruit development; it is self-fertile but pollen from any highbush blueberry species will initiate fruit development.

TABLE I

Aurora Characteristics

| Characteristic | Aurora |
|---|---|
| Bush | |
| Mature height | 1.5 m |
| Mature width | 1.3 m |
| Diameter/width ratio | 1.1 |
| Growth habit | Upright to semi-spreading |
| Annual renewal canes | 5–6 |
| Internode length on spring shoots | 2.5 cm |
| Mature cane color | Greyed-Green (198A) |
| Mature cane length | 1.4 m–1.6 m |
| Mature cane width | 2 cm–4 cm |
| Fall color - new shoots | Patches of Red-Purple (60A) |
| Foliage | |
| Leaf shape | Elliptic - ovate |
| Apex shape | Acute |
| Base shape | Cuniate to truncate |
| Leaf length | 2.5 cm–3.5 cm |
| Leaf width | 1.1 cm–1.5 cm |
| Leaf length/width ratio | 2.1 |
| Leaf serration | Entire |
| Pubescence | None |
| Color - top | Green (137A) |
| Color - bottom | Green (138A) |
| Veination | Palmate |
| Vein color | Green (138B) |
| Petiole length | 4 mm |
| Petiole color | Green (138B) |
| Blossoms | |
| Shape of corolla | Elongate-urceolata |
| Calyx | 5 lobed |
| Style length | At edge of corolla |
| Color of open flower | Mostly white (155D) |
| Flower # per cluster | 8–10 |
| Flower diameter | 5 mm–7 mm |
| Reproductive Organs | |
| Type | Berries with seeds |
| Seed size | 1 mm × 2 mm |
| Number of seeds | 10–50 per fruit |
| Mature Fruit | |
| Length | 1.1 cm–1.3 cm |
| Width | 1.4 cm–1.8 cm |
| Color | (156D) |
| Shape | Globose, uniform |
| Color with bloom | Violet Blue (98A) |
| Color without bloom | Blue (103A) |
| Pedicel scar size | 1.44 mm |
| Pedicel length | 2 cm–3 mm |
| Pedicel color | Green (143B) |
| Average weight | 1.5 gm |

In trials in Michigan and Oregon, Aurora has consistently had better color, was firmer and had a better picking scar than Elliott (Tables II and III). They also had greatly improved flavor. In several post-harvest trials, the relative fruit rot susceptibility of the Elliott and Aurora genotypes was similar and good (Table IV). Aurora had a slightly longer storage life than 'Elliott' in 2001 and 2002. The fruit are eaten fresh, frozen or processed into products like jams, jellies and yogurt.

Aurora is distinguishable from Liberty (co-pending application Ser. No. 10/350,343, filed Jan. 23, 2003) in that Aurora is first harvested 10–14 days after Liberty (mid-August vs. Late August to early September in Michigan). Aurora leaves are entire, while Liberty leaves are serrated. The bush height/width ratio of Aurora is about 1.1, while Liberty's is about 1.4.

Aurora is distinguishable from Draper (co-pending application Ser. No. 10/350,344, filed Jan. 23, 2003) in that Aurora is harvested 6–8 weeks after Draper (mid-August vs. late June to early July in Michigan). The bush height/width ratio of Aurora is about 1.1, while Draper's is about 2.2. Aurora's leaves are elliptic-ovate (leaf/length ratio is >2), while Draper's leaves are narrow elliptic (leaf/length ratio is <2).

TABLE II

Characteristics of mature 'Aurora' in comparison to 'Elliott' at Benton Harbor, MI in 2001 and 2002. All values were the same in both years, except for harvest date. The rating scale was 1–9, with 1–4 = inferior, 5–6 = acceptable, 7 = good, 8 = very good and 9 = superior.

| Traits | Aurora | Elliott |
|---|---|---|
| Horticultural | | |
| Date of first harvest | 8/29 and 9/7 | 8/23 and 8/27 |
| Fruit load | 7 | 8 |
| Size | 7 | 6 |
| Color | 8 | 6 |
| Picking scar | 8 | 7 |
| Firmness | 8 | 7 |
| Flavor | 8 | 5 |
| Taxonomy | | |
| Leaf margin | entire | entire |
| Leaf shape | elliptic-ovate | elliptic |
| Leaf length/width ratio | >2 | <2 |
| Bush diameter/width ratio | 1.1 | 1.4 |
| Fall color on 1-year shoots | red and green | solid red |
| Bark texture - mature wood | rough | rough |

TABLE III

Mean fruit ratings of 'Elliott' and 'Aurora' at Grand Junction, MI, Corvallis, OR and Lowell, OR in 2002. Plants were set as two-year-old rooted cuttings in 2000. Evaluations were made when the bushes were 50% ripe.

| Location | Cultivar | Fruit load | Size | Color | Picking scar | Firmness | Flavor |
|---|---|---|---|---|---|---|---|
| Grand Junction | Elliott | 8[Z] | 6 | 6 | 7 | 7 | 5 |
| | Aurora | 7 | 7 | 8 | 8 | 8 | 8 |

TABLE III-continued

Mean fruit ratings of 'Elliott' and 'Aurora' at Grand Junction, MI, Corvallis, OR and Lowell, OR in 2002. Plants were set as two-year-old rooted cuttings in 2000. Evaluations were made when the bushes were 50% ripe.

| Location | Cultivar | Fruit load | Size | Color | Picking scar | Firmness | Flavor |
|---|---|---|---|---|---|---|---|
| Corvallis | Elliott | 9 | 6 | 7 | 7 | 7 | 6 |
| | Aurora | 8 | 7 | 8 | 8 | 8 | 8 |
| Lowell | Elliott | 9 | 6 | 7 | 7 | 7 | 6 |
| | Aurora | 8 | 7 | 8 | 8 | 8 | 8 |

[Z]The rating scale 1–9, with 1–4 = inferior, 5–6 = acceptable, 7 = good, 8 = very good and 9 = superior.

TABLE IV

Comparison of postharvest storage life and fungal rots of 'Elliott' and 'Aurora' harvested at Benton Harbor, MI. Fruit were picked on the same day, when the bushes were 30–40% ripe.

| Determinations | Elliott | Aurora |
|---|---|---|
| Percentage of fruit rotted[X] | | |
| 2000 | 12% | — |
| 2001 | 12% | 11% |
| 2002 | 10% | 16% |
| Types of fruit rots in 2002[Y] | | |
| Alternaria | 6 | 10 |
| Colletotrichum | 4 | 2 |
| Botrytis | 0 | 0 |
| Storage life (days)[Z] | | |
| 2000 | 7 | — |
| 2001 | 7 | 14 |
| 2002 | 7 | 14 |

[X]Four pints of fruit were evaluated after being held for 3 weeks at 2 C. in zip-lock storage bags. Fungal species were not determined.
[Y]Fifty fruit were randomly selected from 4 pints and held for ten days at room temperature.
[Z]Four pints of fruit were held at 2 C. in plastic zip-lock bags and examined at 7 day intervals. The containers were considered non-salable, if more than a few fruit appeared rotten or >25% were soft to the touch.

What is claimed is:

1. A new and distinct highbush blueberry plant, substantially as illustrated and described herein.

* * * * *

UNITED STATES PATENT AND TRADEMARK OFFICE

CERTIFICATE OF CORRECTION

PATENT NO. : PP15,185 P3
DATED : September 28, 2004
INVENTOR(S) : James F. Hancock It is certified that error appears in the above-identified patent and that said Letters Patent is hereby corrected as shown below:

Column 2,
Line 12, “rood” should be -- root --.
Line 32, “Sargent, K. L.,” should be -- Sargent, K. L. --

Column 3,
Line 26, “below-20” should be -- below -20° --.

Column 4,
Line 56, “3 mm” should be -- 3 cm --.

Signed and Sealed this

First Day of February, 2005

JON W. DUDAS
*Director of the United States Patent and Trademark Office*